United States Patent [19]
Phillips

[11] Patent Number: 5,593,455
[45] Date of Patent: Jan. 14, 1997

[54] PLUG MOUNTED PROSTHESIS

[76] Inventor: Van L. Phillips, 5499 Maravillas, Rancho Santa Fe, Calif. 92067

[21] Appl. No.: 250,016

[22] Filed: May 27, 1994

[51] Int. Cl.$^6$ ............................................. A61F 2/66
[52] U.S. Cl. ................................... 623/47; 623/53
[58] Field of Search ........................... 623/55, 53, 52, 623/38, 47, 50

[56] References Cited

U.S. PATENT DOCUMENTS

| | | | |
|---|---|---|---|
| 808,296 | 12/1905 | Merrick | 623/53 X |
| 2,267,339 | 12/1941 | Paulsen . | |
| 2,453,969 | 11/1948 | Carter . | |
| 2,692,392 | 10/1954 | Bennington et al. . | |
| 2,699,554 | 1/1955 | Comelli . | |
| 2,731,645 | 1/1956 | Woodall | 623/53 |
| 3,422,462 | 1/1969 | Finnieston | 623/38 |
| 3,501,777 | 3/1970 | Degtyarev et al. | 623/55 X |
| 3,800,333 | 4/1974 | Friberg | 623/38 |
| 3,820,169 | 6/1974 | Long et al. . | |
| 3,940,804 | 3/1976 | Benton et al. | 623/55 X |
| 4,007,496 | 2/1977 | Glabiszewski . | |
| 4,089,072 | 5/1978 | Glabiszewski . | |
| 4,128,903 | 12/1978 | Marsch et al. . | |
| 4,314,398 | 2/1982 | Pettersson . | |
| 4,547,913 | 10/1985 | Phillips . | |
| 4,619,661 | 10/1986 | Axelsson . | |
| 4,645,509 | 2/1987 | Poggi et al. | 623/55 |
| 4,688,559 | 8/1987 | Vito et al. | 623/43 X |
| 4,759,110 | 7/1988 | Rieger et al. . | |
| 4,938,776 | 7/1990 | Masinter | 623/49 |
| 4,959,073 | 9/1990 | Merlette | 623/55 |
| 5,156,631 | 10/1992 | Merlette | 623/52 |
| 5,181,932 | 1/1993 | Phillips . | |
| 5,201,775 | 4/1993 | Arbogast | 623/38 |
| 5,326,352 | 7/1994 | Ferrier | 623/38 |
| 5,425,781 | 6/1995 | Allard et al. | 623/38 |

FOREIGN PATENT DOCUMENTS

| | | | |
|---|---|---|---|
| 0030952 | 7/1926 | France | 623/53 |
| 295807 | 12/1916 | Germany . | |
| 0308671 | 10/1918 | Germany | 623/55 |
| 0366553 | 1/1923 | Germany | 623/53 |
| 179844 | 10/1954 | Germany . | |
| 0135800 | 5/1979 | Germany | 623/38 |
| 2718395 | 9/1986 | Germany . | |
| 1454449 | 1/1989 | U.S.S.R. | 623/53 |
| 1600759 | 10/1990 | U.S.S.R. . | |
| 0013078 | of 1889 | United Kingdom | 623/53 |
| 621576 | 4/1949 | United Kingdom . | |
| 1371996 | 10/1974 | United Kingdom . | |
| 2070439 | 9/1981 | United Kingdom | 623/47 |

*Primary Examiner*—David H. Willse
*Attorney, Agent, or Firm*—Knobbe, Martens, Olson & Bear

[57] ABSTRACT

A prosthetic foot adapted to be attached to a standard sized pylon defining a lower surface and an interior surface which defines a cavity. The foot includes a horizontal foot portion, an upstanding ankle portion connected to the foot portion and a plug formed around the upper end of the ankle portion. The plug defines a radially extending flange spaced downward from the top of the plug and a mating portion above the flange.

A mating portion of the plug fits within a cavity defined by the interior surface of the pylon. A layer of adhesive is provided between the interior surface of the pylon and the mating portion of the plug so that the interior surface and mating portion form a tight fit and the layer of adhesive forms an adhesive bond. The adhesive bond resists torsional load and the mating portion of the plug and the pylon cooperate to resist sheer forces.

16 Claims, 6 Drawing Sheets

PLUG MOUNTED PROSTHESIS

FIELD OF THE INVENTION

The present invention pertains to an improved prosthesis and, more particularly, to a prosthetic foot having a improved means for securing the foot to a standard pylon.

BACKGROUND OF THE INVENTION

Prosthetic foot technology has advanced considerably in the past 20 or so years to the point where an amputee has available a wide variety of styles. Key performance considerations include ease and stability of alignment, axial and torsional strength, as well as ease of replacement. That is, it is important that a prosthetic foot maintain both its vertical alignment, as well as resist twisting. Due to the axial compressive forces exerted on the prosthetic device along the alignment axis, the prosthetic device must also have significant axial strength.

While the performance of the prosthetic foot is very important, however, so is the cost. That is, to the extent that the cost renders the prosthetic foot unavailable for use by a given wearer, the performance characteristics of the prosthetic device are irrelevant for that wearer. Accordingly, significant effort has been made to reduce the cost of materials and manufacturing for prosthetic devices.

With most prosthetic devices now in use, the prosthetic device is fitted directly to the amputation socket and once the prosthesis is attached to the socket, it cannot be removed. Any change of prosthesis requires a complete change of the amputation socket along with the prosthesis. The fitting of the prosthesis to the amputation socket requires careful alignment and adjustment and is thus expensive.

One attempt at joining a prosthetic foot to a stump of a wearer is disclosed in U.S. Pat. No. 4,959,073 to Merlette. An upper leg portion is first bonded to a sleeve which fits tightly within a housing. The housing is aligned within the stump and secured with overwraps of composite material. This specialized attachment assembly is not yet in widespread use.

More commonly, a lower leg pylon extends between a stump of the amputee and a prosthetic foot. There are many means for connecting the pylon to the prosthetic foot, typically involving various clamps and fasteners. Such fastening means add weight and can loosen after extended use. Furthermore, the attachment mechanisms presently available require special tools and tightening standards, and introduce small parts which might be damaged or lost.

Thus, there is a need for a simple, inexpensive prosthetic foot which can be securely fastened to standard leg pylons which does not require bulky or inconvenient fastening mechanisms.

SUMMARY OF THE INVENTION

The present invention provides an improved prosthetic device, which is both relatively inexpensive and can be used in connection with standard leg pylon arrangements. Thirty millimeter leg pylons are the industry standard. Preferably, the cylindrical pylons are made from composite, with an outer diameter of 30 millimeters and an inner diameter of 24 millimeters, although alluminum pylons are more common. The improved prosthetic foot includes a horizontal foot portion, an upstanding ankle portion connected to the foot portion and a plug formed around the upper end of the ankle portion. The plug defines a radially extending flange spaced downward from the top of the plug and a mating portion above the flange.

A mating portion of the plug fits within a cavity defined by the interior surface of the pylon. A layer of adhesive is provided between the interior surface of the pylon and the mating portion of the plug so that the interior surface and mating portion form a tight fit and the layer of adhesive forms an adhesive bond. The adhesive bond resists torsional load and the mating portion of the plug and the pylon cooperate to resist sheer forces.

Desirably the plug is made from rigid epoxy which is adhesively bonded to the ankle portion. Additionally, the mating portion of the plug desirably has a length of at least 1½ inches to distribute the force exerted at the bond over a wider area. Further, the adhesive bond will desirably release when the adhesive is heated above 200° F.

To ensure that the prosthetic device can be properly oriented both when being covered by a cosmesis and when being attached to the wearer, a gripping means is provided. Desirably, this gripping means comprises an indention or flat edge, which allows the device to be securely held in a standard clamp.

Another aspect of the invention is a method of manufacturing a prosthetic device including (1) inserting a curable material into a cavity of a mold, the cavity defining a first alignment axis; (2) bringing together a prosthetic element and the mold so that a portion of the prosthetic element is positioned within the cavity of the mold; (3) bringing the portion of the prosthetic element into contact with the curable material; (4) coaxially aligning the axis of the mold and the prosthetic element; (5) curing the curable material so that, when cured, a plug bonded to the portion of the prosthetic element within the mold is formed; and (6) separating the prosthetic element and the material from the mold after the curable material has cured. Desirably, the method also includes the step of curing the material such that the plug defines a radial flange.

The present invention provides an improved means for connecting a prosthetic foot and a leg pylon. The attachment device comprises a plug which closely conforms around an upwardly extending ankle portion of the prosthetic foot. Preferably, the plug is molded around the ankle portion to provide the close fit and a tight bonding therebetween. The plug has an exterior surface which closely conforms to an interior surface of the downwardly depending leg pylon. Preferably, the pylon is tubular and the plug is cylindrical with a lower annular ledge upon which the pylon rests. In a preferred embodiment, the exterior surface of the plug is adhesively bonded to the interior surface of the pylon. The prosthetic foot may be replaced by heating up the adhesive between the plug and the leg pylon to loosen it, a replacement plug and prosthetic foot being then inserted into the pylon and adhered thereto.

DESCRIPTION OF THE PREFERRED EMBODIMENTS

Figure 1:
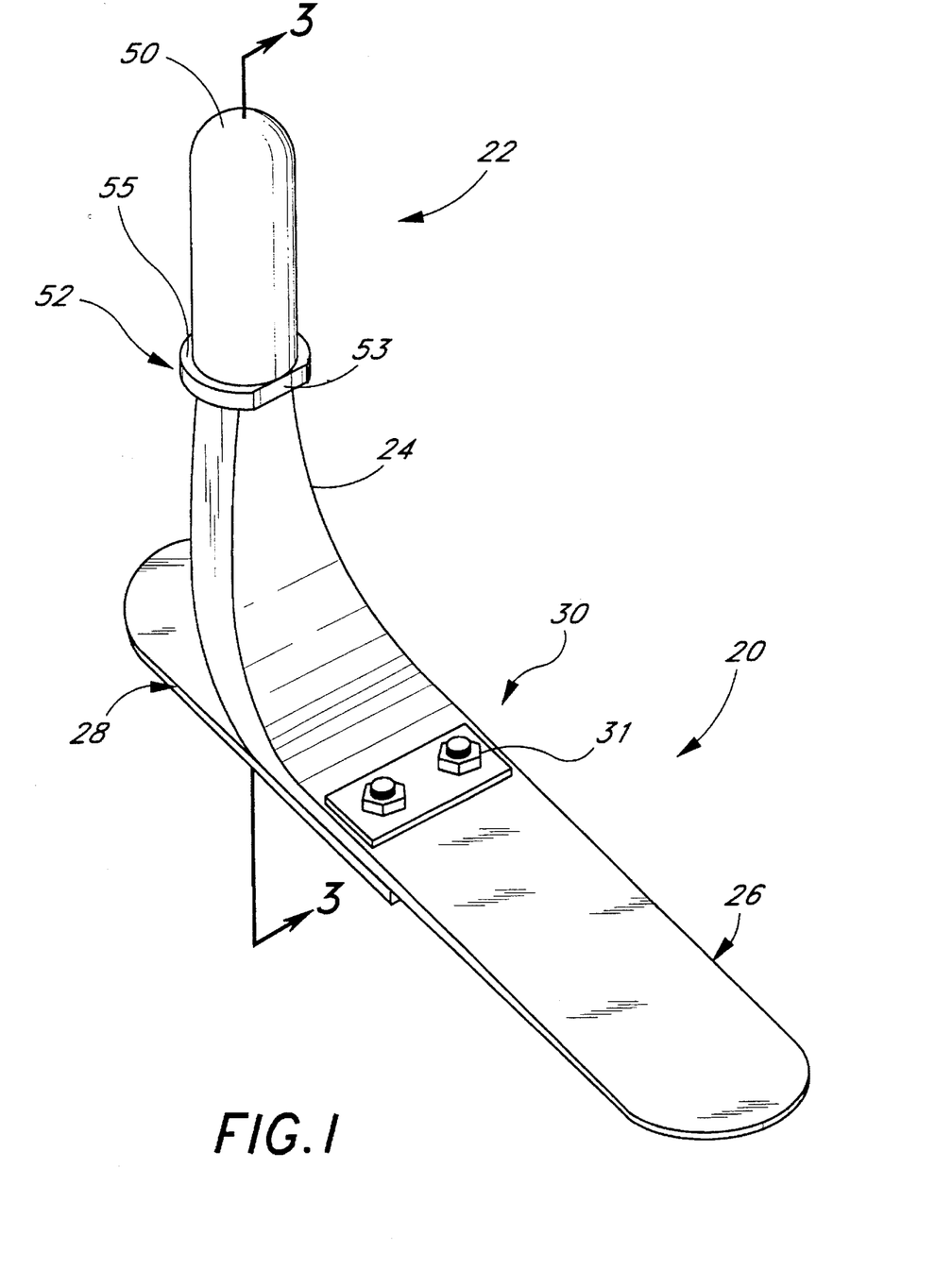
FIG. 1 is a perspective view of a prosthetic foot having an attachment plug of the present invention thereon.

FIG. 1 shows a prosthetic foot 20 having an attachment plug 22 formed on an upwardly extending ankle portion 24. The prosthetic foot 20 generally comprises a two-part construction having an ankle/foot member 26 attached to a heel member 28 via a fastener plate assembly 30 including fasteners 31. In other embodiments, the prosthetic foot 20 may be formed of a single piece, or the members may be joined by other means, such as adhesive bonding. The prosthetic foot 20 is secured to a downwardly depending leg pylon 32 (shown in phantom in FIG. 3).

As is known to those of skill in the art, the tubular structure of the pylon provides both narrow width and tremendous strength and stiffness. Importantly, the use of the standard 30 millimeter pylon provides for low material costs and, as the pylon need not be molded in any way, low manufacturing costs.

Figure 2:
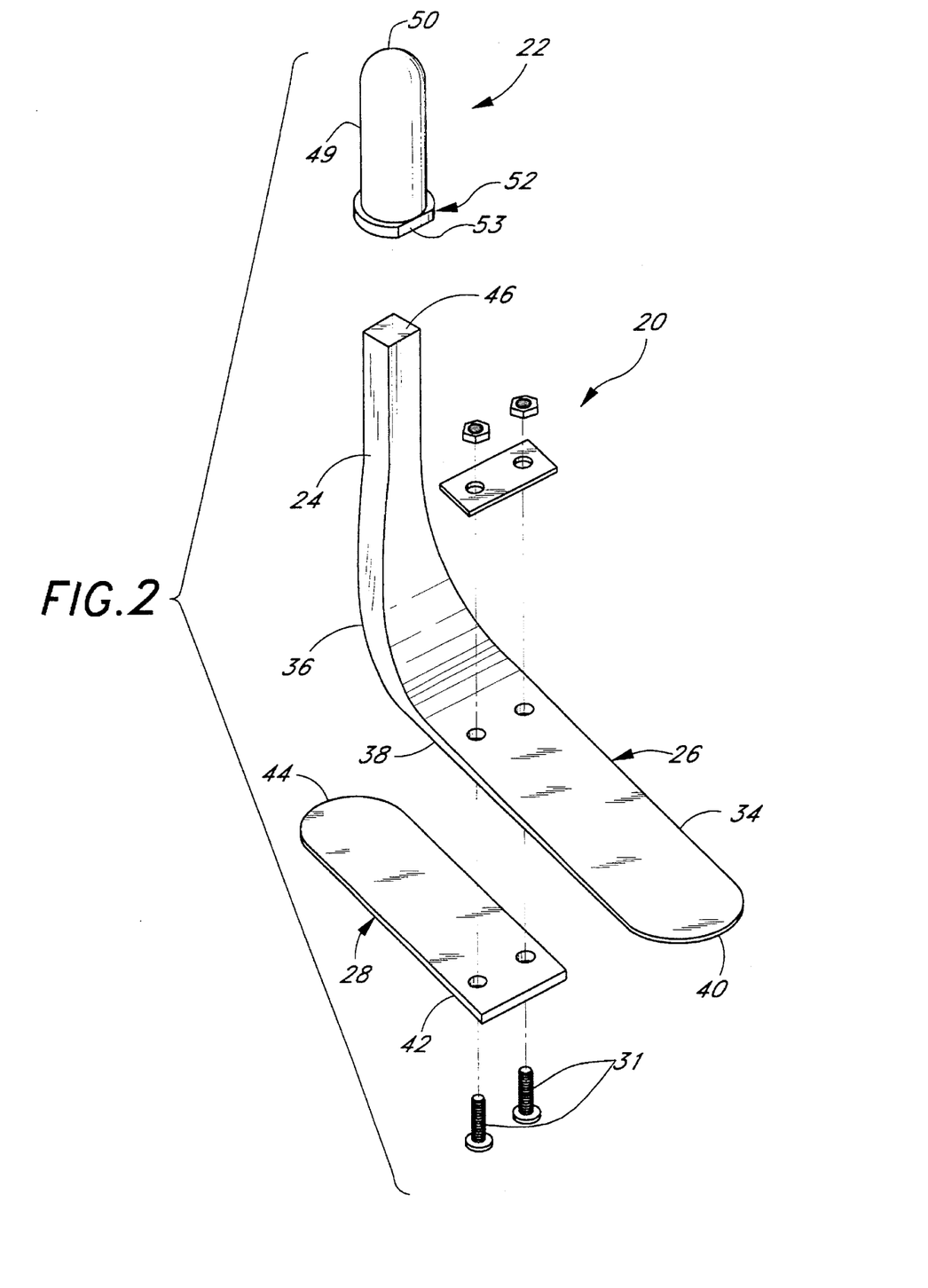
FIG. 2 is an exploded view of the prosthetic foot and attachment plug of FIG. 1.
Figure 3:
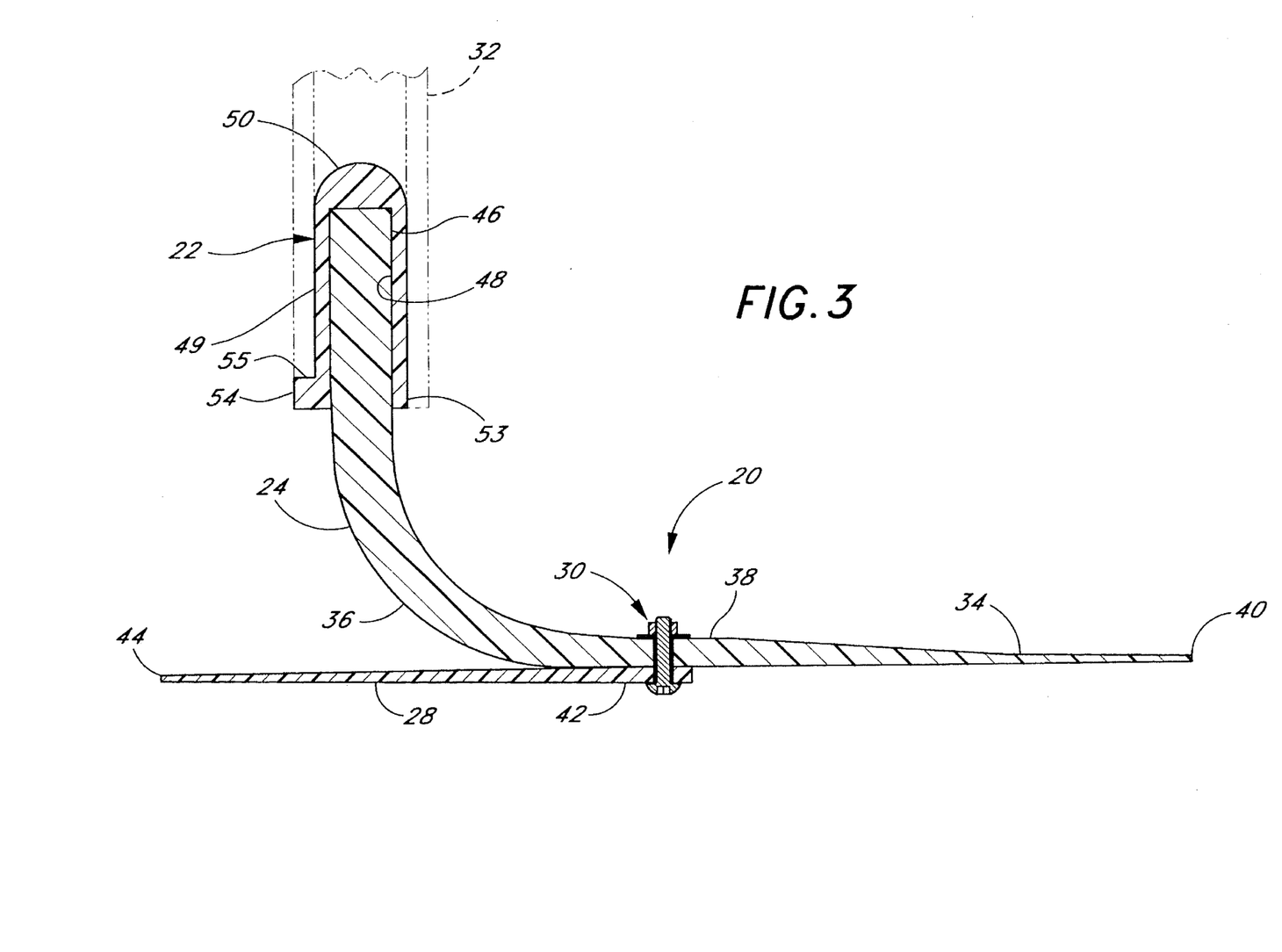
FIG. 3 is a cross-sectional view of the attachment plug on the prosthetic foot taken along line 3—3 of FIG. 1.

Now with reference to FIG. 2, the ankle/foot member 26 comprises the aforementioned ankle portion 24 and a plate-like front foot portion 34. A curvilinear flexure region 36 forms a transition between the ankle region 24 and front foot region 34. The flexure region 36 gradually tapers thinner in height toward the front foot portion 34. As seen in FIG. 3, a heel connecting region 38 remains relatively thick, and the front foot portion terminates in a thin tip 40 which provides flexibility for the forward end of the prosthetic foot. Likewise, the heel member 28 tapers from a connecting region 42 to a rear tip 44 for reasons of flexibility.

The flexure region 36 and ankle portion 24 exhibit a gradual change in shape from the plate-like front foot portion 34 to an upper, generally square cross section terminal end 46. The cross section of the terminal end 46 is relatively constant for the portion around which the attachment plug 22 fits. As seen best in FIG. 3, the terminal end 46 fits within a generally square cross section cavity 48 in the attachment plug 22.

In addition to defining the aforementioned square cross section cavity 48, the attachment plug 22 has a cylindrical outer surface 49 terminating in a dome-shaped top 50. The attachment plug 22 also defines a radially outwardly extending lower annular flange 52 having an upper surface 55 which provides a stop for the downwardly depending leg pylon 32. Preferably, the outer perimeter 54 of the flange 52 is sized approximately the same as the outer diameter of the leg pylon 32 to be flush therewith. A front flat 53 is formed to facilitate subsequent mold assembly of an outer foot-shaped cosmesis (not shown). The flat 53 provides an orientation surface for a clamp to hold the prosthetic foot 20 properly aligned within the cosmesis mold.

Figure 4:
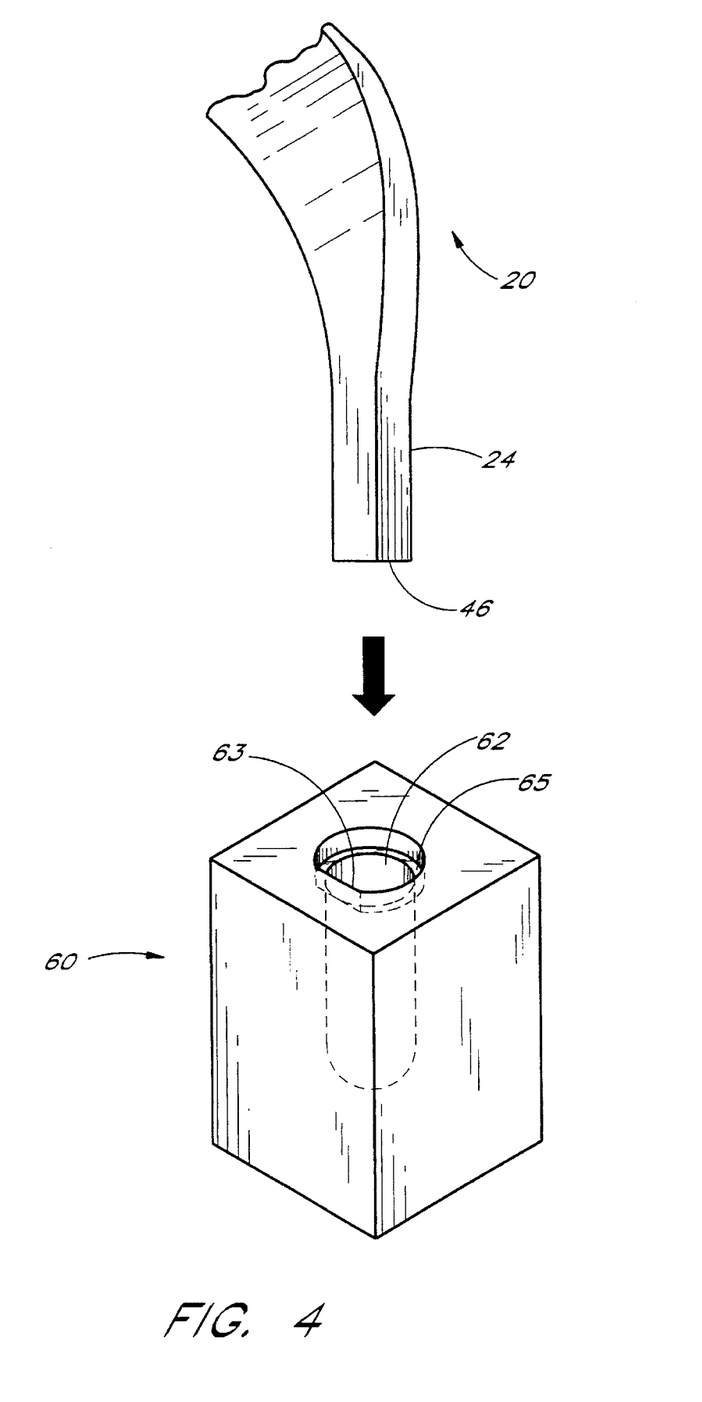
FIG. 4 is a perspective schematic view of a prosthetic foot prior to being inserted into a mold for forming an attachment plug.
Figure 5:
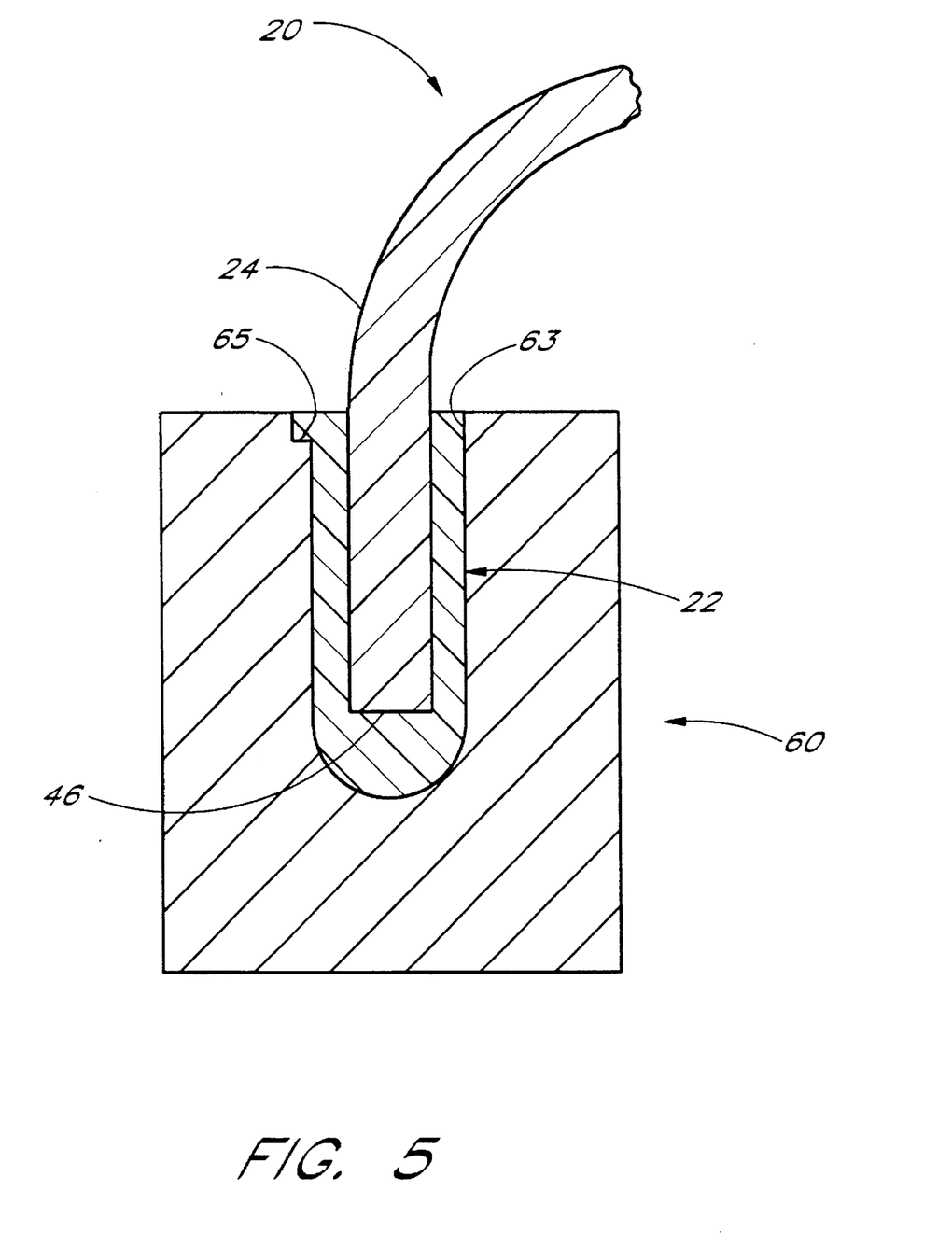
FIG. 5 is a cross-sectional view of a prosthetic foot within the mold of FIG. 4.

To construct the prosthetic foot 20 having the attachment plug 22, a female mold having the external shape of the plug 22 is filled with a casting epoxy in a liquid state. FIG. 4 schematically depicts a mold 60 including a mold cavity 62 shaped like the exterior of the attachment plug. A flat portion 63 in an upper cylindrical step 65 forms the flat 53 in the flange 52. The prosthetic foot 20 (partially shown) is lowered so that the terminal end 46 fits concentrically within the mold cavity 62, as best seen in FIG. 5, to provide an even amount of plug material therearound. Either before or after lowering the foot 20, the desired plug material in liquid form is added to the cavity 62. The plug material is then allowed to harden, whereupon the bonded assembly of the foot 20 and plug 22 is removed from the mold, or the mold removed from the plug. The molding of the attachment plug 22 around the terminal end 46 of the ankle/foot member 26 ensures a precise fit and a secure bond between the attachment plug and the ankle/foot member. The assembled foot 20 and plug 22 can mate with a variety of leg pylons 32 having a solid tubular shape as shown, or a discontinuous wall structure. There are numerous ways to accomplish such a molding operation, and only one is shown. For example, the mold cavity 62 may be enclosed and the liquid epoxy injected therein.

Figure 6:
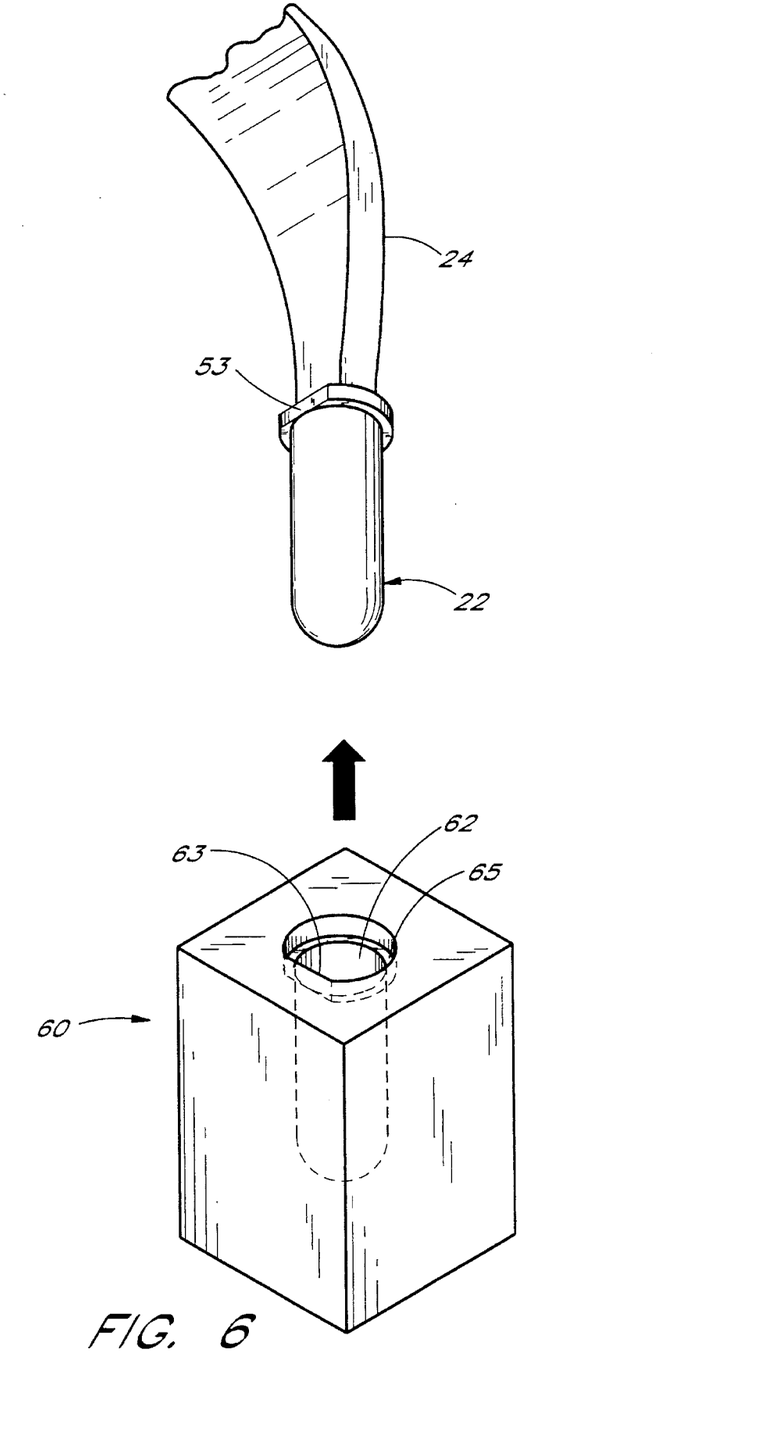
FIG. 6 is a perspective schematic view of a prosthetic foot after being removed from the attachment plug mold.

Subsequent to lowering the foot 20, the foot is held in place while the urethane dries and/or cures to a solid state. Preferably, the cavity 62 is made of self-lubricating material or has external lubrication so that the foot 20 and plug 22 can be pulled directly out of the cavity, as depicted in FIG. 6. In the alternative, the mold 60 may be made in two or more pieces to enable it to be split to release the plug 22.

The leg pylon 32 is connected to the plug 22 by means of an adhesive applied to the exterior of the plug, or to the interior of the pylon. Desirably, the outer mating surface 49 is sized such that when the attachment plug 22 is inserted into the open end of the pylon, it forms a friction fit as well as, after the adhesive has been allowed to dry and cure, an adhesive bond. The adhesive is preferably a low melting temperature adhesive so that the pylon 32 and plug 22 may be separated upon subsequent application of heat. In other words, if a wearer chooses to replace the prosthetic foot 20, it is a relatively simple matter to heat up the exterior of the pylon 32 at the region of the plug 22 and loosen the adhesive therebetween. The particular adhesive used preferably liquifies at less than 350° F. and, more preferably, the adhesive liquifies between 200°–250° F.

The plug may be formed of a casting epoxy with particles of graphite therein for added strength. In the preferred embodiment, the material of the plug 22 has a minimum strength in solid form to withstand the bending and compressive forces imparted on it in use. Furthermore, the material must be compatible with the particular foot material 20 and leg pylon material 32. In other words, the material of the plug 22 should be chosen so as not to create corrosion or other weakening or detrimental phenomenon with the material of either the foot 20 or pylon 32. The material of the foot 20 can be laminated graphite-fiber composite, fiberglass, or other suitably strong and lightweight materials as are well known in the prosthetic foot art.

Desirably, the mating portion of the plug 22 (i.e., that portion above the flange) has a length of at least one and, preferably, at least one and one-half inches, so as to reduce the effective shear force experienced by the plug by creating a longer lever arm within the pylon. This length also results in a larger surface area over which to apply adhesive, so that a stronger adhesive bond can be created to resist torsion (i.e., twisting about the alignment axis, usually the axis of the pylon).

Importantly, due to the stiffness of the standard 30 millimeter pylon, the prosthetic foot described better replicates the natural movement of the foot, leg and ankle. That is, the pylon is extremely stiff, as is the shin bone, so that bending occurs below the bottom of the pylon, in the ankle and, to a lesser extent, the foot regions. Furthermore, because the standard shape of the pylon need not be altered, manufacturing costs and rejected parts are kept to a minimum.

Although this invention has been described in terms of certain preferred embodiments, other embodiments that are apparent to those of ordinary skill in the art are also in the range of the invention. Accordingly, the scope of the invention is intended to be defined only by reference to the following claims.

I claim:

1. A prosthetic foot adapted to be attached to a rigid tubular pylon defining a lower interior attachment surface, comprising:

a horizontal foot portion comprising a spring-like support member;

an upstanding ankle portion connected to said horizontal foot portion, said ankle portion defining an axis and having an upper attachment end having a generally rectangular cross-section;

a plug fixedly secured to said upper attachment end of said ankle portion having a substantially closed top and a substantially open bottom, said plug defining a radially extending flange spaced downward from said top of said plug, said plug further having a generally rectangular inner surface or cavity sized to closely receive said upper attachment end of said ankle portion and an outer surface generally corresponding to a mating inner surface of said tubular pylon, the inner and outer dimensions of said plug being sized so that said plug and said attachment end of said ankle portion fit tightly within one end of said tubular pylon, said flange having sufficient strength to resist downward axial loads exerted on said flange by said pylon when said prosthetic foot is worn.

2. The prosthetic foot of claim 1, wherein said mating surface of said plug is cylindrical.

3. The prosthetic foot of claim 2, wherein said plug is formed from graphite reinforced epoxy.

4. The prosthetic foot of claim 3, wherein said mating surface of said plug has a length of at least one and one-half inches.

5. The prosthetic foot of claim 4, wherein said flange further comprises gripping means for facilitating gripping and orientation of said plug and said foot.

6. The prosthetic foot of claim 1, wherein said mating surface of said plug has a length of at least one and one-half inches.

7. The prosthetic foot of claim 6, wherein said flange further comprises gripping means for facilitating gripping and orientation of said plug and said foot.

8. A lower limb prosthesis, comprising:

a horizontal foot portion comprising a spring-like support member;

an upstanding ankle portion connected to said horizontal foot portion, said ankle portion defining an axis and having an upper end;

a substantially rigid plug being formed around and fixedly secured by polygonal interlocking means to said upper end of said ankle portion, said plug defining a radially extending flange spaced downward from the upper end of said upstanding ankle portion and a mating portion above said flange, said flange defining an upper surface;

a standard 30 mm hollow tubular pylon defining a lower annular surface which abuts said upper surface of said flange whereby downward axial loads exerted on said pylon are resisted by said flange, said pylon further comprising a substantially vertical tubular interior surface which closely receives and is bonded to said mating portion of said plug, said interior surface forming a tight fit with said mating portion of said plug and wherein said upstanding ankle portion extends into said hollow tubular pylon, said mating portion of said plug and said pylon cooperating to resist axial and torsional shear forces.

9. The lower limb prothesis of claim 8, wherein said pylon is cylindrical.

10. The lower limb prothesis of claim 9, wherein said mating portion of said plug is cylindrical.

11. The lower limb prothesis of claim 10, wherein said plug is formed from graphite reinforced epoxy.

12. The lower limb prothesis of claim 11, wherein said plug is adhesively bonded to said ankle portion.

13. The lower limb prothesis of claim 12, wherein said mating portion of said plug has a length of at least one and one-half inches.

14. The lower limb prothesis of claim 13, wherein said adhesive bond will release when said adhesive is heated above 200 degrees Fahrenheit.

15. The lower limb prothesis of claim 14, wherein said flange further comprises a gripping means for allowing said plug and upstanding ankle portion to be securely gripped and orientated.

16. The lower limb prothesis of claim 15, wherein said gripping means comprises a flat side.

* * * * *

UNITED STATES PATENT AND TRADEMARK OFFICE
Certificate

Patent No. 5,593,455

Patented: January 14, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Van L. Phillips, Rancho Santa Fe, CA; and Roland Christianson, Fayette, UT.

Signed and Sealed this Twenty-sixth Day of August 2003.

CORRINE M. MCDERMOTT
*Supervisory Patent Examiner*
Art Unit 3738